United States Patent
Cross, III

(10) Patent No.: US 11,612,632 B2
(45) Date of Patent: *Mar. 28, 2023

(54) COMPOSITIONS AND METHODS FOR TREATMENT OF PREDIABETES

(71) Applicant: William H. Cross, III, Waco, GA (US)

(72) Inventor: William H. Cross, III, Waco, GA (US)

(*) Notice: Subject to any disclaimer, the term of this patent is extended or adjusted under 35 U.S.C. 154(b) by 843 days.

This patent is subject to a terminal disclaimer.

(21) Appl. No.: 15/496,919

(22) Filed: Apr. 25, 2017

(65) Prior Publication Data

US 2018/0303896 A1    Oct. 25, 2018

(51) Int. Cl.
| | | |
|---|---|---|
| A61K 38/05 | (2006.01) | |
| A61K 31/385 | (2006.01) | |
| A61K 31/353 | (2006.01) | |
| A61K 36/87 | (2006.01) | |
| A61K 31/145 | (2006.01) | |
| A61K 31/198 | (2006.01) | |
| A61K 31/155 | (2006.01) | |
| A61K 31/593 | (2006.01) | |
| A61K 31/714 | (2006.01) | |
| A61K 31/047 | (2006.01) | |
| A61K 31/4172 | (2006.01) | |
| A61K 45/06 | (2006.01) | |
| A61K 31/185 | (2006.01) | |
| A61K 31/07 | (2006.01) | |

(52) U.S. Cl.
CPC .......... *A61K 38/05* (2013.01); *A61K 31/047* (2013.01); *A61K 31/07* (2013.01); *A61K 31/145* (2013.01); *A61K 31/155* (2013.01); *A61K 31/185* (2013.01); *A61K 31/198* (2013.01); *A61K 31/353* (2013.01); *A61K 31/385* (2013.01); *A61K 31/4172* (2013.01); *A61K 31/593* (2013.01); *A61K 31/714* (2013.01); *A61K 36/87* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,711,602 | A | 1/1973 | Herschler |
| 5,719,119 | A | 2/1998 | Veech |
| 7,060,295 | B2 | 6/2006 | Richardson |
| 7,645,742 | B2 | 1/2010 | Stohs |
| 9,414,615 | B2 | 8/2016 | Sridhar |
| 10,945,979 | B1 | 3/2021 | Schroeder |
| 2001/0011083 | A1 | 8/2001 | Barr |
| 2001/0031744 | A1 | 10/2001 | Kosbab |
| 2005/0129783 | A1 | 6/2005 | McCleary |
| 2011/0313043 | A1 | 12/2011 | Kramer |
| 2012/0232003 | A1 | 9/2012 | Takahashi |
| 2014/0044685 | A1 | 2/2014 | Greenberg |
| 2016/0228409 | A1 | 8/2016 | Cross, III |
| 2017/0312329 | A1 | 11/2017 | Cross, III |

FOREIGN PATENT DOCUMENTS

| | | |
|---|---|---|
| CN | 101716182 | 4/2013 |
| IN | 1306CHE2007 | 1/2009 |
| WO | 2008048045 | 4/2008 |
| WO | 2013108262 | 7/2013 |

OTHER PUBLICATIONS

Lautt, et al., Can. J. Physiol. Pharmacol., 88:313. (Year: 2010).*
Henriksen, E.J., Free Radical Biology & Medicine, 40:3. (Year: 2006).*
U.S. Appl. No. 15/650,825, filed Jul. 2017, Cross, William H. III.*
Bell, D.S.H., 2012, Case Report in Endocrinology, Article ID 165056, 3pp.
Curtis, L., 2013, International Journal of Diabetes Research, 2:56-60.
Hagen, M. et al., 2017, Current Medical Research and Opinion, 33(9):1623-1634.
Henriksen, E.J., 2006, Free Radical Biology & Medicine, 40:3-12.
Lautt et al., 2010, Can. J. Physiol. Pharmacol., 88:313-323.
Shinohara, T. et al., 2004, J. Biol. Chern., 279:23559-23564.
Vita Sciences, Nervex Neuropathy Pain Relief (Product Literature), Jan. 26, 2017.
Wagner, T., 2012, Pain Management, 2(3):239-250.
Wojtczak, A., 2002, Medical Teacher, 24:658-660.
Yonguc, et al., 2015, Gene, 555:119-126.
McCarty, M.F., 2017, Healthare, 5, 28pp (doi:10.3390/healthcare5010015).
U.S. Appl. No. 15/017,527, 20160228409, Aug. 11, 2016.
U.S. Appl. No. 15/650,825, 20170312329, Sep. 6, 2019.
U.S. Appl. No. 16/264,595, 20190231806, Aug. 1, 2019.
U.S. Appl. No. 16/264,609, 20190231807, Aug. 1, 2019.
U.S. Appl. No. 16/264,614, 20190231725, Aug. 1, 2019.
U.S. Appl. No. 16/283,660, 20190275154, Sep. 12, 2019.
U.S. Appl. No. 17/352,674.

* cited by examiner

*Primary Examiner* — Michael Barker
(74) *Attorney, Agent, or Firm* — Thomas | Horstemeyer LLP

(57) ABSTRACT

The invention provides compositions and methods to treat prediabetes. In particular, the invention has discovered that particular combinations of diverse types of antioxidants have synergistic and surprising effects for use against prediabetes. The diverse types of antioxidants include: antioxidants that comprise stabilizing heteroatoms; antioxidants with conjugated segments of alternating single and double bonds; antioxidants with disulfides; and antioxidants with phenolic groups. In particularly useful embodiments one or more of the antioxidants that comprise stabilizing heteroatoms have pro-oxidant effects, e.g., in the liver.

6 Claims, No Drawings

COMPOSITIONS AND METHODS FOR TREATMENT OF PREDIABETES

FIELD OF THE INVENTION

The invention concerns compositions and methods for the treatment and prevention of prediabetes.

BACKGROUND

Prediabetes is a condition characterized by abnormally high yet less than extreme blood sugar levels, (i.e., in the range of 100 to 125 mg/dL). Prediabetic patients lack one or more symptoms that characterize diabetes, however but the condition is often a prelude to type 2 diabetes mellitus (T2DM). A quarter of the cases commonly progress to T2DM within 3 to 5 years, and half within 10 years. Prediabetes may be identical to metabolic syndrome, however the latter is evaluated by a different set of biomarkers.

A common symptom of prediabetes is impaired fasting glucose (IFG), in which blood sugar levels are high but still below those typical of diabetes. Many IFG patients retain normal responses to a glucose tolerance test. Another common system is impaired glucose tolerance (IGT) associated with insulin resistance and elevated cardiovascular risk. Among American adults over 40 years of age, 33% have IFG, 15% have IGT, and 40% are prediabetic (i.e., they have IFG and/or IGT).

Despite those diagnostic conditions the symptoms of prediabetes are often not distinctive. Thus a range of signs are monitored: persistent hunger; obesity; weight gain or at the other extreme, unexplained weight loss; flu-like weakness and fatigue; blurry vision; slowness of healing for cuts and bruises; tingling or insensate extremities; and recurring infections of the skin, gums, bladder or vagina.

Prediabetes is associated with many possible causes beyond high blood sugar, and these range from sleep disorders, genetics, cardiovascular disease, hypertension, high triglyceride levels, low HDL cholesterol, elevated weight, pregnancy, high birth weight, polycystic ovarian syndrome.

The lifestyle intervention guidelines to prevent the onset of type 2 diabetes include: dietary regimes that are low in sugar, refined carbohydrates, saturated fats, salt and total calories; regular physical exercise, for instance 30 minutes per day five days per week; and weight reduction even by as little as a few percent.

The prevalence of prediabetes remains high despite widespread medical monitoring and health education, and methods to treat it have been lacking apart from the lifestyle changes just discussed. Consequently there is an ongoing need for compositions to treat and prevent 5 prediabetes.

SUMMARY OF THE INVENTION

The invention provides compositions and methods to treat and prevent development of prediabetes. In particular, the present invention has discovered that particular combinations of 10 diverse types of antioxidants that have synergistic and surprising effects for use against prediabetes. The diverse types of antioxidants include: antioxidants that comprise stabilizing heteroatoms; antioxidants with conjugated segments, i.e., segments in which double bonds alternate with single bonds; antioxidants with disulfide bonds; and antioxidants with phenolic groups. It has further been discovered that it is beneficial to use antioxidants that facilitate an oxidative balance, i.e., that have pro-oxidant effects, e.g., in the liver.

Particularly suitable compositions for the invention include a combination of each of the ingredients indicated in Table I.

TABLE I

| | |
|---|---|
| Taurine in a range of 40-360 mg; a non-limiting illustrative quantity is 200 mg. Taurine is an antioxidant that comprises a stabilizing heteroatom, relieves oxidative stress, and has a pro-oxidative effect in the liver. | 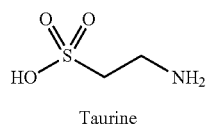<br>Taurine |
| Beta-alanine in a range of 10-90 mg; a non-limiting illustrative quantity is 50 mg. Beta-alanine is an anti oxidant that comprises a stabilizing heteroatom. | 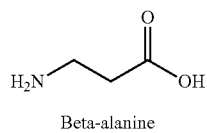<br>Beta-alanine |
| Acetyl-L-carnitine in a range of 20-180 mg; a non-limiting illustrative quantity is 100 mg. Acetyl-L-carnitine is an antioxidant that comprises a stabilizing heteroatom, relieves oxidative stress, and has a pro-oxidative effect in the liver. | 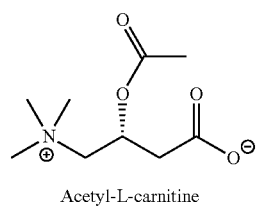<br>Acetyl-L-carnitine |
| Agmatine in a range of 25-225 mg; a non-limiting illustrative quantity is 125 mg. Agmatine is an antioxidant that comprises a stabilizing heteroatom. | 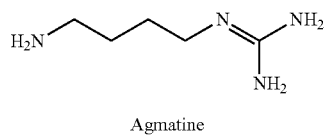<br>Agmatine |

TABLE I-continued

| | |
|---|---|
| Grape seed extract in a range of 10-90 mg; a non-limiting illustrative quantity is 50 mg. Grape seed extract comprises phenolic antioxidants, such as for instance, (−)-epicatechin and oligomers of (−)-epicatechin. | 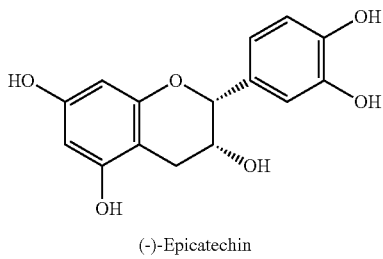 [SMILES: Oc1cc(O)c2c(c1)O[C@H](c1ccc(O)c(O)c1)[C@H](O)C2]<br>(−)-Epicatechin |
| L-carnosine in a range of 5-45 mg; a non-limiting illustrative quantity is 25 mg. L-carnosine is an antioxidant that comprises a stabilizing heteroatom, and is active against reactive organic species (ROS) radicals. | 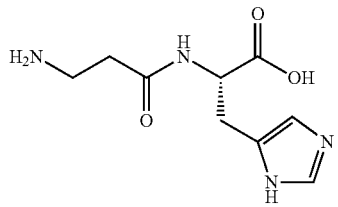<br>L-carnosine |
| Vitamin D3 in a range of 500-4500 I.U.; a non-limiting illustrative quantity is 2500 I.U. Vitamin D3 is an antioxidant with conjugated hydrocarbon segments. | 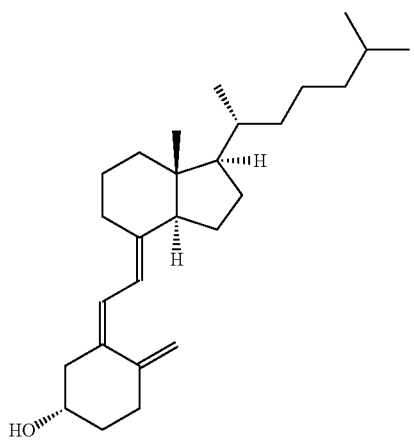<br>Vitamin D3 |

TABLE I-continued

Methylcobalamin (a form of Vitamin B12), 20-220 μg; a non-limiting illustrative quantity is 120 μg. Methylcobalamin is an antioxidant that comprises a conjugated segment; the segment contains nitrogen atoms and among other properties can bind the oxidant nitric oxide (NO).

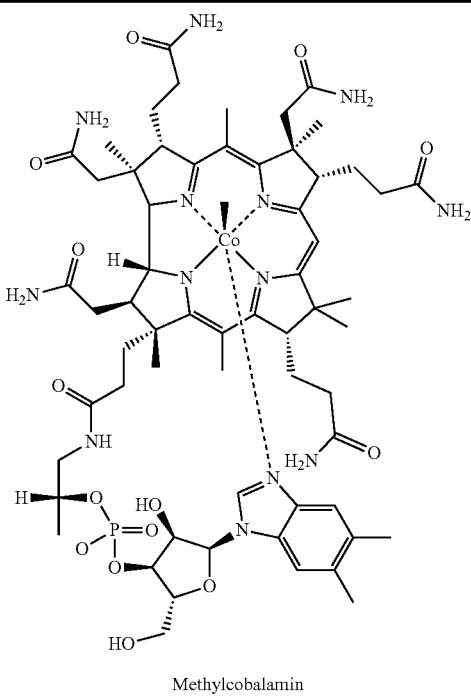

Methylcobalamin

In particular embodiments compositions of the invention include a combination of each of the ingredients indicated in both Tables I and II.

TABLE II

Lutein in a range of 1-9 mg; a non-limiting illustrative quantity is 5 mg. Lutein is an antioxidant with conjugated hydrocarbon segments.

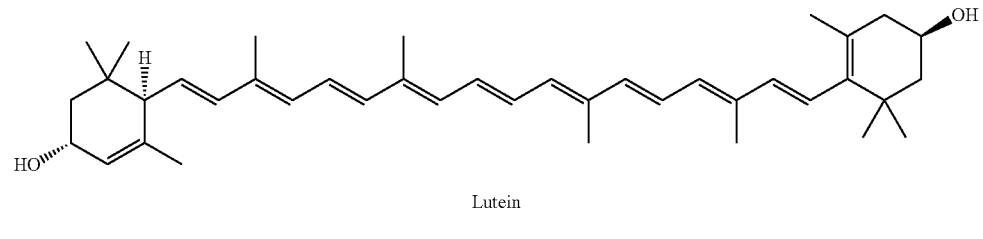

Lutein

Alpha-Lipoic Acid in a range of 50-450 μg; a non-limiting illustrative quantity is 500 μg. Alpha-Lipoic Acid is a disulfide-type antioxidant

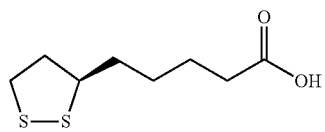

Alpha-Lipoic Acid

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A method for treatment of prediabetes comprising administration of a composition comprising taurine, beta-alanine, acetyl-L-carnitine, agmatine and L-carnosine;

b) at least one of the antioxidant compounds selected from the group consisting of vitamin D compounds, cobalamin compounds and carotenoids;

c) at least one of the antioxidant compounds selected from the group consisting of alpha-lipoic acid; and d) at least one of the antioxidant compounds selected from the group consisting of epicatechin and oligomers of epicatechin;

wherein:
the amount of the composition is effective to reduce or mitigate at least one symptom of prediabetes.

2. The method of claim 1 wherein the antioxidant b) consists of vitamin D3, methylcobalamin, and lutein.

3. The method of claim 1 wherein epicatechin and the oligomers of epicatechin are provided in the form of grape seed extract.

4. The method of claim 1 wherein the composition comprises:
   a) taurine in an amount selected from the range of 40 to 360 mg;
   b) beta-alanine in an amount selected from the range of 10 to 90 mg;
   c) acetyl-L-carnosine in an amount selected from the range of 20 to 180 mg;
   d) agmatine in an amount selected from the range of 25 to 225 mg;
   e) grape seed extract in an amount selected from the range of 10 to 90 mg;
   f) L-carnosine in an amount selected from the range of 5 to 45 mg;
   g) vitamin D3 in an amount selected from the range of 500 to 4,500 I.U.; and
   h) methylcobalamin in an amount selected from the range of 20 to 220 µg.

5. The method of claim 1 wherein the composition further comprises:
   a) lutein in an amount selected from the range of 1 to 9 mg; and
   b) alphalipoic acid in an amount selected from the range of 100 to 900 µg.

6. The method of claim 1 wherein the composition comprises:
   a) taurine in an amount of 200 mg;
   b) beta-alanine in an amount of 50 mg;
   c) acetyl-L-carnosine in an amount of 100 mg;
   d) agmatine in an amount selected of 125 mg;
   e) grape seed extract in an amount of 50 mg;
   f) L-carnosine in an amount of 25 mg;
   g) vitamin D3 in an amount of 2,500 I.U.;
   h) methylcobalamin in an amount of 120 µg;
   i) lutein in an amount of 5 mg; and
   j) alphalipoic acid in an amount of 500 µg.

* * * * *